United States Patent
McNeirney et al.

[11] Patent Number: 6,146,333
[45] Date of Patent: Nov. 14, 2000

[54] ACOUSTIC FERTILITY MONITOR AND DETECTOR

[75] Inventors: John C. McNeirney, Fairburn, Ga.; John D. Borchers, III, Petaluma, Calif.; William H. Burns, Jr., Orchard Park, N.Y.

[73] Assignee: Fertility Acoustics Inc., Buffalo, N.Y.

[21] Appl. No.: 09/198,772

[22] Filed: Nov. 24, 1998

Related U.S. Application Data

[63] Continuation of application No. PCT/US98/16422, Aug. 7, 1998.

[60] Provisional application No. 60/055,562, Aug. 13, 1997.

[51] Int. Cl.$^7$ ..................................................... A61B 10/00
[52] U.S. Cl. ............................................................. 600/551
[58] Field of Search ...................................... 600/551, 559

[56] References Cited

U.S. PATENT DOCUMENTS

| | | | |
|---|---|---|---|
| 4,024,499 | 5/1977 | Bosscher | 340/146.2 |
| 4,038,496 | 7/1977 | Feezor | 179/1 N |
| 4,201,225 | 5/1980 | Bethea et al. | 128/746 |
| 4,284,847 | 8/1981 | Besserman | 179/1 N |
| 4,556,069 | 12/1985 | Dalton et al. | 128/746 |
| 4,773,428 | 3/1988 | Wong et al. | 128/738 |
| 4,884,447 | 12/1989 | Kemp et al. | 73/585 |
| 5,209,238 | 5/1993 | Sundhar . | |

OTHER PUBLICATIONS

Circadian and menstrual rhythms in frequency variations of spontaneous otoacoustic emissions from humans Hearing Research, 58 (1992) 1992 Elsevies Science Publishers BV; Research School of Biological Sciences, Australian National University, Cahberaa, Australia (Andrew Bell).

Menstrual Rhythms in Sensory Processes: A Review of Fluctuations in Vision, Olfaction, Audition, Taste, and Touch–PsychologicalBulletin 1983, vol.93, No. 3; pp. 539–544(Mary Brown Parlee) Graduate School and University Center, City University of New York.

C.R. Soc. Biol., 1982, 176, 184–189. Neurophysfologie. Audiometrie fonctionnelle chez la femme en phase preovulaloire et en phase mensiruelle, (par J.C. Petiot et J. Parrot), Laboratoire de PsychophysiologieAppliquee, Faculte des Sciences, 6, boulevard Gabriel, 21000 Dijon, Frrance.

*Primary Examiner*—Max Hindenburg
*Assistant Examiner*—Brian Szmal
*Attorney, Agent, or Firm*—Hodgson, Russ, Andrews, Woods & Goodyear LLP

[57] ABSTRACT

The present invention relates to a non-invasive method and device for detecting hormonal changes in humans by monitoring and detecting changes in psycho-acoustic sensitivity of humans. In particular, the onset of ovulation in a female, preceded by a sudden increase in the level of luteinizing hormone (LH) in the blood stream, is predicted by measuring various psycho-acoustic responses of the female in certain frequency ranges. The measured psycho-acoustic responses include monaural and binaural audio interpretation.

38 Claims, 3 Drawing Sheets

ACOUSTIC FERTILITY MONITOR AND DETECTOR

This application is a continuation of international application number PCT US/98/16422, filed Aug. 7, 1998, pending.

CROSS-REFERENCE TO A RELATED APPLICATION

Applicants hereby claim priority on earlier filed provisional patent application Ser. No. 60/055,562, filed Aug. 13, 1997, which is incorporated herein by reference.

BACKGROUND OF THE INVENTION

1. Field of the Invention

The present invention relates to a method and apparatus for determining ovulation state and predicting ovulation in females and particularly to a non-invasive method and apparatus for determining the onset of hormonal changes in humans based on detection of changes in psycho-acoustic response of the human body to sound.

2. Prior Art

Some physiological changes in humans are preceded by a sudden increase in the level of certain hormones. One such change, the onset of ovulation in women, is preceded by a sudden increase in the level of luteinizing hormone (LH) in the blood stream. This LH concentration increase, or surge, begins approximately 36 hours to 48 hours preceding ovulation, peaks about 18 hours prior to ovulation and ends at the time of ovulation. The surge primarily results in expulsion of the egg from the ovum after the receptors of the ovaries become affected by the increased concentration of LH. The increased levels of LH, and other accompanying hormonal changes, cause several physiological and psychological changes to occur. The term "psycho-acoustic" is used herein to refer to these changes, i.e., changes which do not appear to be related to physical changes in the ear, but appear to be related to the way sound is sensed by the central nervous system. The term "ovulation state" is used herein to refer to the present physiological and psycho-acoustic state of a woman in relation to the time ovulation will occur in her. The term "pre-ovulatory" is used to refer to that ovulation state which exists during the time period beginning 36 to 48 hours prior to ovulation and ends around the time of ovulation. The term "non pre-ovulatory" refers to the time period which falls outside the pre-ovulatory time period.

Different methods of indication of changes in female physiological characteristics before and during her menstrual cycle are currently used in clinics to determine the onset of the ovulation. For example, increased concentrations of LH can be detected in a woman's urine during the LH surge. Other physiological changes in a woman, such as basal body temperature, changes in vaginal mucus secretions and cervical surface texture, also occur near the time of the ovulation. Reliance on these natural indicators of ovulation is subjective and often requires extensive training to assess. Moreover, urine and blood-based ovulation tests are primarily performed in clinics, even though some home urine test kits are available on the market. Currently, to perform the most reliable ovulation test—an LH level increase measurement—a clinical analysis of venous blood is required. This procedure is expensive, since a blood sample must be processed in a laboratory and assistance of a trained clinician is usually necessary.

Furthermore, because of the delays associated with lab testing, the predictive fertile window (the 5-day period preceding ovulation) is greatly reduced, which, in turn, reduces the probability of impregnation. Additionally, the LH surge detection in blood or urine often requires multiple tests. At-home urine test kits are quite expensive, priced from $20 per package, and contain only 5 test strips per kit. In addition, there are other disadvantages associated with at-home urine testing due to a large number of factors that alter the test's accuracy. Being the blood's filtrate, urine contains elevated LH concentrations during the pre-ovulatory surge; these concentrations can be detected using a urine analysis. However, such at-home urine testing is not entirely dependable, because the test results are reliable only when conducted at certain times of the day. For example, the first urine in the morning can not be reliably analyzed, as the LH concentration within it is altered, skewing test results. Additionally, it can take up to 12 hours after the LH surge in the blood for detectable levels of the hormone to collect in the urine, thus reducing the predictive fertility window. Another disadvantage of at-home urine tests lies in their inability to adjust the scale per specific physiological parameters of an individual. Furthermore, the test results are affected by pharmaceuticals and common chemicals like soap. Finally, detection of an LH surge usually requires multiple testing which increases costs.

Invasive methods of ovulation detection, such as, for example, radioimmunoassay, require a homogenized blood serum. However, since radioimmunoassay measures both beta subunits and LH, it is not an entirely reliable LH indicator. A radioreceptor assay method measures only LH-blood serum concentrations and produces more reliable results. Nevertheless, the assay required either a homogenized blood or urine serum for testing, thus, decreasing the predictive fertile window because of the delay lab testing requires.

Therefore, because of the number of unreliable factors, conditions and expenses associated with clinical, serum, or at-home urine testing, a more reliable, easy to operate ovulation indicator used at the convenience of an individual will be beneficial in fertility assessment.

It is known that two significant psycho-acoustic changes take place in correlation with a woman's ovulation cycle. It has been documented that sound perception inside the ear occurs by two different means of audio interpretation, namely, monaural and binaural beat interpretation. Monaural interpretation occurs when an individual hears a tone at the same frequency in both ears and perceives the vibrations as sound. Usually an individual can detect sounds in the frequency range between 20 and 20 000 Hz. Binaural audio interpretation occurs when two tones of frequencies differing by 3–6 Hz sound in different ears. Under normal conditions an individual utilizes central summation to combine the two tones and perceive the resulting sound as the average of the two different frequencies. This phenomenon produces a warbling effect and is perceived as a roving sound throughout the head.

Hearing sensitivity changes, i.e., changes in hearing threshold, to sounds in certain frequency ranges have been observed to correlate with the preovulatory state. During the LH surge a female loses 30–35 dB of hearing and becomes less sensitive or unable to perceive as many frequencies as she would normally perceive. However, her range of sound interpretation shifts, so she becomes capable of interpreting a greater number of tones at lower frequencies, typically tones in the range of about 6 000 Hz to about 14 000 Hz.

It has been discovered that a change in monaural and binaural perception occurs in females during the preovulatory period. For example, just before ovulation and menstruation females experienced a significant decrease in their abilities to measure absolute pitch.

In order to be detected by a woman during the onset of ovulation (the pre-ovulatory state), the volume, or intensity of sounds in the general range of about 6 000 Hz to about 14 000 Hz must be increased by about 10 dB to about 40 dB above the volume, or intensity at which she can detect these sounds at other times during her ovulation cycle. Therefore, by detecting and measuring this change in hearing sensitivity the ovulation state of the woman can be determined, and the time of ovulation predicted.

Loss of the ability to synthesize binaural beats is another psycho-acoustic change which has been observed to correlate to the preovulatory state. It has been discovered that the female loses the ability to discern warbling effect within certain frequency ranges during the 24-hour period before ovulation during the LH cycle. The usual form of binaural hearing occurs when two tones differing by about 3 to 6 Hz are presented to the human ear, one tone to each ear. For example, if a tone of 600 Hz is presented to one ear and a tone of 603 Hz is presented to the other ear, the central nervous system synthesizes a warbling tone.

The psycho-acoustic phenomenon of binaural beat synthesis is most noticeable at beat frequencies below 1000 Hz and the phenomenon becomes quite distinct in the frequency range of about 400 Hz to 800 Hz. By sensing the presence and, subsequently, the loss of this ability to hear the warbling sound, the onset of the increase in LH and other accompanying hormonal changes preceding ovulation can be detected and the probable time of ovulation predicted.

Knowledge of her ovulation state can be used by the woman for birth control purposes, i.e., to increase or decrease the probability of conception. There has been a long felt need for an effective, non-invasive method and means for determining ovulation state and predicting the time of ovulation.

SUMMARY OF THE INVENTION

Accordingly, it is an object of the present invention to provide a method and device for detecting the onset of the pre-ovulation or ovulation stage in a female by monitoring hearing sensitivity patterns known to be indicative of the female ovulation cycles. The monitoring capabilities offered by the present invention offer a user cost savings, convenience and accuracy.

It is another object of the present invention to measure the degree of changes in hearing sensitivity to determine the ovulation state and predict the onset of ovulation.

It is also an object of this invention to provide a device for detecting and measuring hearing sensitivity threshold by using various audiometric techniques.

In one embodiment of the present invention a single pure tone within the general frequency range of about 6000 Hz to about 14000 Hz is generated and broadcast, and the hearing threshold of a woman to this tone is detected. Generation of tones and measurement of the threshold response of a woman may be accomplished using known audiometric methods and techniques. The threshold value thus obtained is then compared to reference threshold values.

The term "reference threshold value" is used herein to refer to either of the following. Reference threshold values may be one or more values previously obtained from the subject being tested. The term "reference threshold value" may also refer to one or more values statistically determined to represent a typical or average subject in a particular ovulation state.

By comparing present threshold values to reference threshold values, significant loss of sensitivity may be detected. Further, the degree of such loss may be ascertained and evaluated to more precisely determine the ovulation state of the woman and to predict the time of ovulation.

The preferred method of comparison is a sequential comparison method. According to this method the sensitivity, or threshold response of a subject is measured at predetermined intervals using standard audiometric techniques. The measurements thus obtained may be recorded on a chart or graph, but preferably are stored in the memory of a computer or microprocessor and used to form baseline or reference threshold measurements to which subsequent measurements obtained from the subject are compared. In other words, the most recent threshold value obtained is compared to previous values such that tendencies toward increase and/or decrease in sensitivity can be detected, future values predicted, and present status ascertained. Well known mathematical statistical analysis, filtering techniques and computer programs may be used to process the measurements in the manner just described. When a significant reduction in sensitivity is detected, i.e., the reduction is greater than can be accounted for by normal fluctuations or measurement error, it is likely that the preovulatory state.

DETAILED DESCRIPTION OF THE INVENTION

Figure 2:
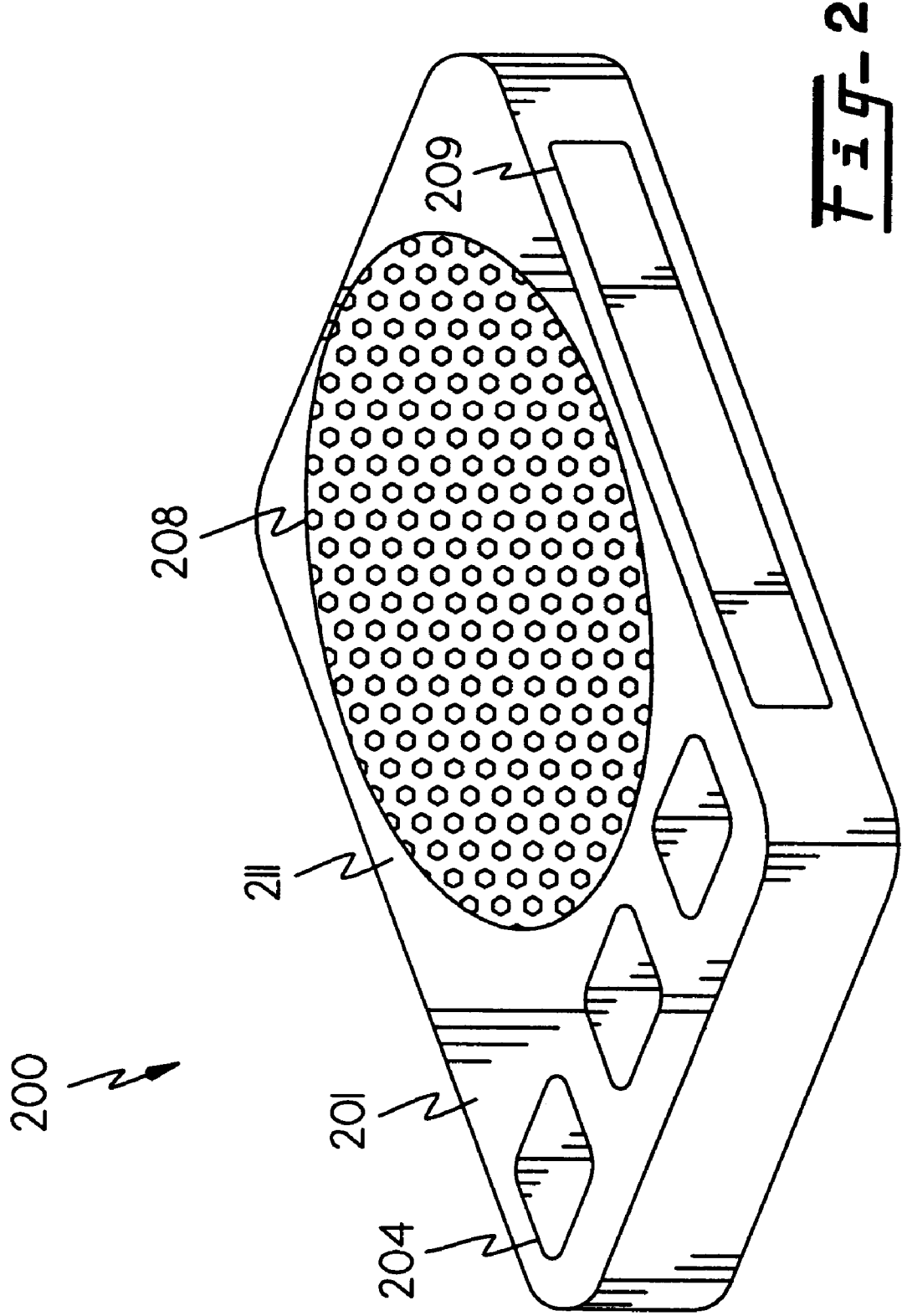
FIG. 2 shows an apparatus for determining ovulation state based on detection of loss of hearing sensitivity according to the principles of the present invention.

FIG. 2 shows a device 200 for detecting ovulation state by measuring monaural hearing sensitivity. Device 200 comprises housing 201 within which is housed audiometric means 211 (not visible in FIG. 2 but illustrated diagrammatically in FIG. 3 at 311). Audiometric means 211 comprises well known audiometric circuits for measuring hearing sensitivity in the frequency range of interest and capable of providing an output representative of the measurements taken. In particular, audiometric means 211 comprises a tone generator, broadcast circuitry which allows the tone or tones to be broadcast at varying intensity levels and control circuitry. The tone generator preferably is capable of producing pure tones in the frequency range from about 5000 Hz to about 16000 Hz. The intensity levels of broadcasting circuitry range from about 3 dB to about 40 dB. The control circuitry causes the tone or tones to be repeated at discreet loudness levels. Audiometric means 211 also comprises means for signalling 209 and means 208 for delivering audible tones. In the presently preferred embodiment, means for signalling 209 is an on-off switch or button located on housing 201. However, alternative means for signalling will be readily apparent to those skilled in the art. Such means include, but are not limited to, remote on-off switches and voice activated on-off switches. Presently preferred means for delivering audible tones 208 is a speaker capable of performing in the frequency range of interest. Alternative means for delivering audible tones 208 include headsets, ear phones or a telephone.

Device 200 further includes display means 204 located on housing 201. In the preferred embodiment display means 204 displays a representation of the ovulation state of the subject being tested. This representation may be numerical, alphanumerical, graphical or pictorial. The presently preferred embodiment includes an alphanumerical display.

The measurements can be done using a single pure tone in the frequency range of interest, or by sequentially presenting tones of different frequency in the range. If tones of different frequencies are used, the sequence may be ascending, descending or a mixed presentation. The reduction in sensitivity (or the increase in the hearing threshold) can be determined by using classic, well-established audiometric methods, using specially designed devices suited for a particular application or by any other means of presenting tones in the desired frequency range at varying levels of loudness. The reduction in hearing sensitivity is determined by repeatedly comparing the current sensitivity to the sensitivity measured in the range from about 6000 Hz to about 14000 Hz during the period preceding the onset of the increase in the level of LH. When the measurement shows a reduction in hearing sensitivity (or an increase in the hearing threshold) which is greater than a normal measurement error, it is highly likely that the increase in the LH level preceding ovulation has begun. After the increase in the LH level has been detected, the most likely time for ovulation can be predicted.

In the preferred embodiment of the invention the device 200 is used by holding it to the ear and depressing and holding down the on-off buttons 209. In this design, the tone generator produces a four tone sequence as follows: 600 Hz, 8000 Hz, 10000 Hz and 12000 Hz each for 3 seconds.

The intensity of the tones in the sequence is adjusted for the normal increase in hearing threshold with increasing frequency. The 600 Hz tone, which can be easily heard by humans, is a prompting tone and also serves to assure the use that device 200 is functioning. The control circuitry repeats the tone sequence ten times, beginning at about 3 decibels and increasing the intensity of the high frequency tones by 3 decibels for each repeat of the sequence. The intensity of the 600 Hz prompting tone is held constant.

When the user hears the high frequency tones, the on-off button 209 is released. The device counts the number of times the sequence is repeated until it is heard. This count is displaced as a 0–9 in the right LED display window. The device stores the current count in memory. The memory also contains the counts for the two previous uses of the device. These are also displayed in the middle and left LED display windows. If the count pattern is ascending then it indicates an increase in hearing threshold for tones in the frequency range presented, therefore, indicating an LH surge.

Other tone patterns are equally usable as are tone presentation durations and sequences.

Figure 1:
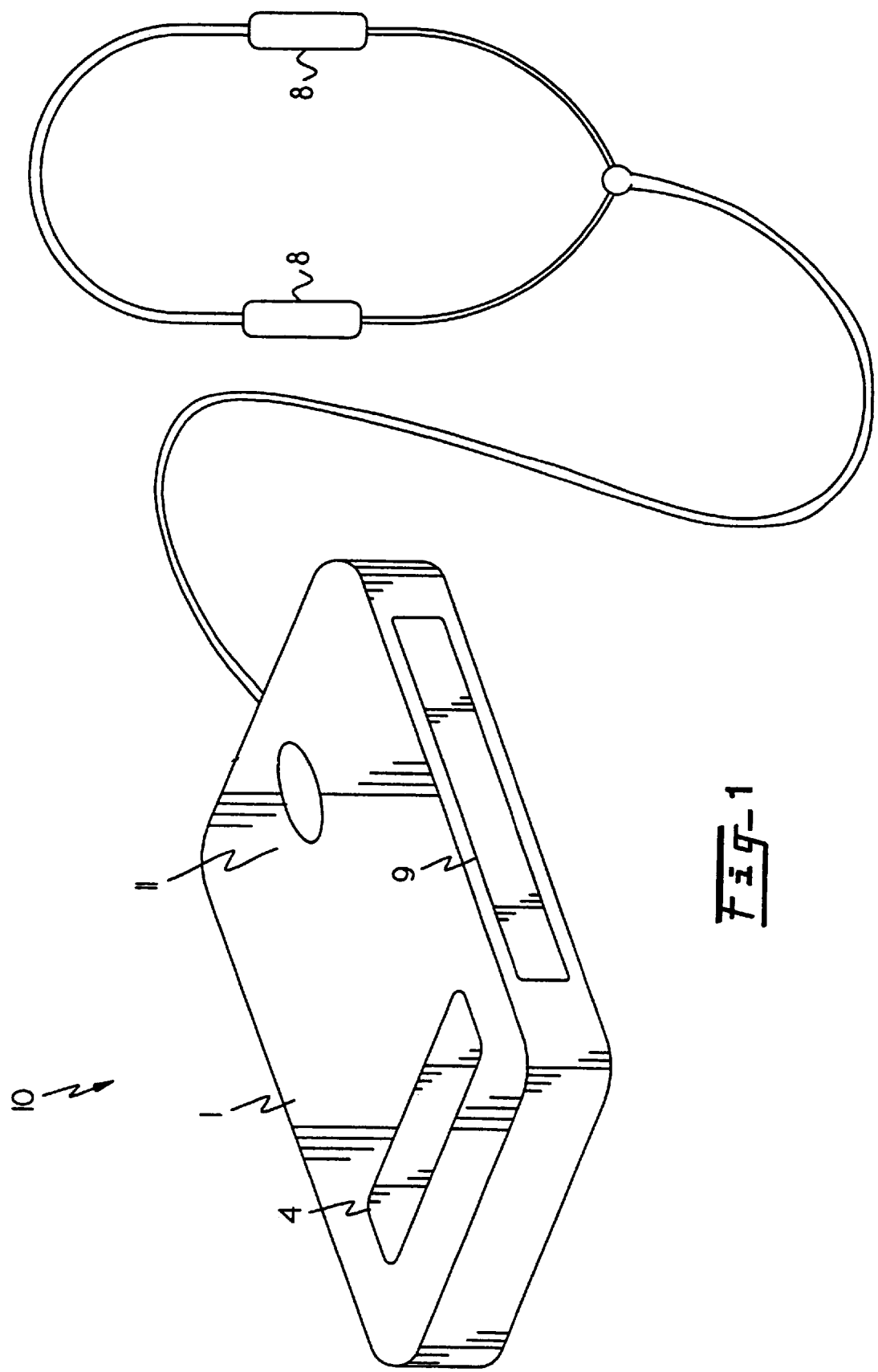
FIG. 1 shows an apparatus for determining ovulation state based on detection of binaural beat synthesis ability according to the principles of the present invention.

FIG. 1 shows a device 10 for determining ovulation state by measuring binaural beat synthesis ability constructed according to the principles of the present invention. Binaural beat synthesis ability can be measured using pairs of pure tones in the 100 Hz to 1000 Hz frequency range. A first tone of a preselected tone pair is presented to one ear of a woman, and the second tone of the preselected tone pair is presented to the other ear. Each pure tone in a tone pair is selected from the frequency range of 100 Hz to 1000 Hz such that the first tone of the pair differs in frequency from the second tone of the pair by about 1 Hz to about 60 Hz. More than one tone pair may be presented to a woman. Either the higher or lower tone in the tone pair may be presented to either the right or the left ear.

A measurement of the binaural beat synthesis ability of the subject is then made using standard audiometric techniques well known in the art. According to the teachings of the present invention, the measurements thus obtained are compared to non-preovulatory ability to synthesize binaural beats. By detecting and comparing present ability to known reference values, the increase in LH and other hormonal changes preceding ovulation can be detected. An indication of the present ovulation state of the woman can be obtained and provided to her, or to the operator of the device. Further, a prediction of the time of ovulation of the woman can be provided.

Figure 3:
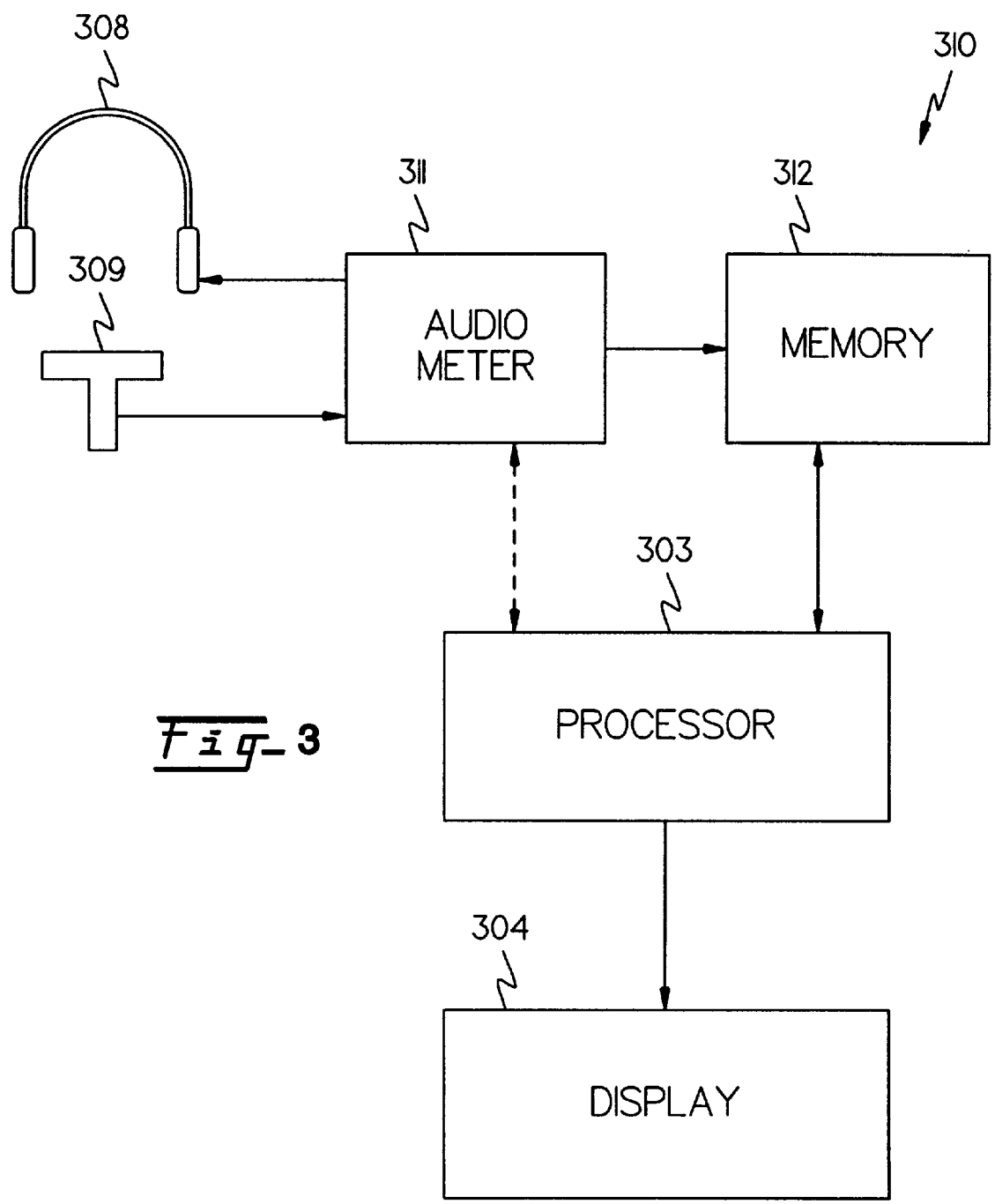
FIG. 3 shows a block diagram of a preferred embodiment of the present invention.

Device 10 comprises housing 1 within which is housed audiometric means 11 (not visible in FIG. 1 but illustrated diagrammatically in FIG. 3 at 311). Audiometric means 11 comprises well known audiometric circuits for measuring binaural beat synthesis ability in the beat frequency range of interest, and capable of providing an output representative of the measurements taken. In the preferred embodiment, the device comprises a tone generator capable of producing pure tones in the range of about 100 Hz to about 1000 Hz frequency range and an earphone set capable of reproducing the generated tones. The device produces one tone at one frequency and the second tone at another frequency, outputting these tones to the stereo earphones, one pure tone to each earphone.

Audiometric means 11 also comprises means for signalling 9 and means for delivering audible tones 8. In the presently preferred embodiment, means for signalling 9 is an on-off switch or button located on housing 201. However, alternative means for signalling will be readily apparent to those skilled in the art. Such means include, but are not limited to, remote on-off switches and voice activated on-off switches. Presently preferred means for delivering audible tones 8 is a stereo headset capable of performing in the frequency range of interest and simultaneously delivering two tones of differing frequency to the ears of the subject. Alternative means for delivering audible tones 8 include other types of ear phones, and possibly, a dual speaker arrangement.

Device 10 may further include display means 4 located on housing 1. Display means 4 may display a representation of the ovulation state of the person being tested. This representation may be numerical, alphanumerical, graphical or pictorial.

The preferred method of using the device comprises placing the earphones in the ears and depressing and holding down the on-off button. If the user experiences the psycho-acoustic binaural beat phenomena, the LH surge and accompanying other hormonal changes preceding ovulation have not begun. If the user, having experienced the phenomena before, loses the psycho-acoustic ability to synthesize binaural beats, it is highly likely that the LH surge and other accompanying hormonal changes have begun, and the onset of ovulation can be predicted.

Any device capable of presenting pure tones stereophonically to the ears can be used to assess the presence or absence of the binaural beat phenomena.

FIG. 3 is a block diagram of a device 310 for determining ovulation state according to the principles of the present invention. Device 310 is the block diagram representation of devices 10 and 200, and shows the interrelation of major components of these embodiments.

Both device 10 and device 200 comprise audiometric means, as indicated at 311. Audiometric means 311 includes means for signalling 309, and means 308 for delivering audible tones to a woman within the frequency range of interest. In the case of hearing threshold measurements the frequency range of interest is from about 6000 Hz to about 14000 Hz. In the case of measurements of binaural beat synthesis ability the desired frequency range is preferably between about 100 Hz and about 1000 Hz with a difference in beat frequencies between about 1 Hz and 60 Hz. In one embodiment of the invention audiometric means 311 is capable of measuring both binaural beat synthesis ability and hearing threshold of the subject. Audiometric means 311 includes an output means for outputting the results of the above-described measurements. The results of the above-described measurements may be provided to a memory 312 and may also be provided to a processor 303.

Memory 312 stores the output of audiometric means 311, and also is configured to store reference values and measurements. Memory 312 is in communication with processor 303. Processor 303 compares the output of audiometric means 311 with the reference values previously obtained and stored in memory 312. Processor 303 makes a determination as to the ovulation state of the subject under test by comparing the output of audiometric means 311 with the stored reference values.

An output of processor 303 is in communication with display device 304 which provides an indication of the ovulation state of the subject under test. This indication may be displayed in numeric, alphanumeric, pictorial or graphical form.

In the simplest embodiment of the present invention, display device 304 allows the presentation of an audiogram output from audiometer 311, that is to say of the sound level as a function of the frequency corresponding to the hearing threshold, or binaural beat synthesis ability of the subject. The ovulation state of the subject may then be determined manually by comparing the audiogram thus obtained to a reference audiogram which has been determined to represent known ovulation states, i.e., pre-ovulation, ovulation, post ovulation, etc. The reference audiogram may be unique to the specific subject being tested, and may be derived from one or more readings previously obtained over the course of that subject's ovulation cycle. Alternatively, the reference audiogram may represent typical or average audiogram values, known to correlate to the ovulation cycle for a given population of subjects.

In the preferred embodiment however, the determination of ovulation state described above is performed automatically by processor 303. The results of the ovulation state determination are then output from processor 303 to display device 304. Processor 303 may be programmed by conventional means to implement the general algorithm of: first accepting the output of the audiometer means; then comparing the output of the audiometer means to the predetermined, prestored audiometric values, i.e., a reference audiogram stored in memory 312; then making a determination as to ovulation state based the comparison; and finally providing the results to display device 304.

Display device 304 may incorporate an LED display, an LCD display, or any of a number of digital or analog displays and indicators. Display device 304 may also be an audio indicator which provides digitized, synthesized or recorded voice messages relating to ovulation status. Display device 304 may also provide a graphical representation of the output of processor 303, as in a typical chart recorder of a type well known in the art.

Accordingly, audiometric means 311 may be a standard audiometer means purchased off-the-shelf. Alternatively, custom audiometric means may be utilized which are adapted to conform to the preferred small size, light weight characteristics, and the frequency range of interest, for the apparatus of the present invention.

In communication with audiometric means 311 is means 308 for delivering audible tones to one or both ears of a subject. Means 308 for delivering audio tones preferably comprises stereo earphones or headphones. Stereo speakers or headphones are the presently preferred means for measuring binaural beat synthesis response. However, one or more speakers may be effective as an alternative means for delivering audio tones to the subject, especially for the purpose of measuring hearing threshold response.

The apparatus of the present invention further includes a signalling device 309, which is also in communication with audiometric means 311. Signalling 309 can be activated by the subject in response to the tones delivered by means 308 for delivering audio tones to a subject such that the hearing threshold of the subject may be determined. In a preferred embodiment signalling device 309 is an on-off switch, or button, which is activated by the subject in response to the presentation of audio tones. Alternate signalling device 309 may include an audio input circuit responsive to voice signals from the subject. Other signalling devices will be readily apparent to those skilled in the art and remain within the scope of the present invention.

It is also contemplated by the scope of the present invention that storing, comparing, displaying and processing data, such as, for example, magnitudes of sound intensities, signals, measured responses and other data, can be performed by a computer.

It is intended that the above description of preferred embodiments of the structure of the present invention and the description of its operation are but one or two enabling best mode embodiments for implementing the invention. Other modifications and variations are likely to be conceived of by those skilled in the art upon a reading of the preferred embodiments and a consideration of the specification. These modifications and variations still fall within the breadth and scope of the disclosure of the present invention.

What is claimed is:

1. A method of detecting a change in a psycho-acoustic sensitivity of a user caused by a hormonal concentration change in the user indicative of onset of a physiological event, comprising the steps of:

generating a sequence of tones, the sequence comprising tones of different intensities;

providing a number of sequences of different sound intensities to the user and receiving a signal from the user indicating the current magnitude of sound intensity of the sequence at which the user hears the sequence; and utilizing the signal from the user indicative of a change in the psycho-acoustic sensitivity of the user to detect a change in hormonal concentration in the user indicative of onset of a physiological event.

2. The method of claim 1, further comprising storing the magnitudes of sound intensity and observing a difference between the current magnitude of sound intensity and the prestored magnitude of sound intensity, the difference being indicative of a change of the psycho-acoustic sensitivity of the user corresponding to a change in the hormonal concentration.

3. The method of claim 2, further including displaying a current visual indication corresponding to the current magnitude of sound intensity of the sequence and displaying a previous visual indication corresponding to a prestored magnitude of sound intensity.

4. The method of claim 3, wherein at least one step is performed by a computer.

5. The method of claim 1, wherein the sequence comprises one tone.

6. The method of claim 1, further comprising storing the current magnitude of sound intensity in a memory.

7. The method of claim 1, wherein the signal from the user comprises operating an on-off button.

8. The method of claim 1, wherein the sound intensity of a successive sequence played to the user is greater that the sound intensity of a previous sequence.

9. The method of claim 1, wherein the psycho-acoustic sensitivity is a monaural hearing sensitivity.

10. The method of claim 1, wherein the change in hormonal concentration is the change in LH concentration.

11. The method of claim 1, wherein the step of providing utilizes a telephone, a headset or ear phones.

12. The method of claim 1, wherein the sequence of tones is generated in a frequency range from about 6000 Hz to about 14000 Hz.

13. A method of detecting a change in a psycho-acoustic sensitivity of a user caused by a hormonal concentration change in the user indicative of onset of a physiological event, the method comprising the steps of:
generating a first and a second tones of different frequencies;
providing the tones to the user in such a way that one ear of the user receives the first tone and the second ear of the user receives the second tone;
receiving a signal from the user indicating a change in ability of the user to synthesize binaural beats; and
utilizing the signal to sense the presence or absence of a change in the psycho-acoustic sensitivity corresponding to a change in the hormonal concentration indicative of onset of a physiological event.

14. The method of claim 13, wherein different frequencies of the first and the second tones are below about 1000 Hz.

15. The method of claim 14, wherein the first and the second tones are propagated at frequencies between about 400 Hz to about 800 Hz.

16. The method of claim 13, wherein the psycho-acoustic sensitivity is binaural audio sensitivity.

17. The method of claim 13, wherein the frequencies of the first and the second tone differ by about 3 to about 6 Hz.

18. The method of claim 13, wherein the psycho-acoustic sensitivity is a binaural hearing sensitivity.

19. The method of claim 13, wherein the change in hormonal concentration is the change in LH concentration.

20. The method of claim 13, wherein at least one step is performed by a computer.

21. A method of detecting a change in a psycho-acoustic sensitivity of a user caused by a hormonal concentration change in the user indicative of onset of a physiological event, the method comprising the steps of:
generating an audio output having predetermined characteristics;
applying the audio output to the user;
detecting a change in hearing ability of the user; and
utilizing the results of the detecting to ascertain the change in hormonal concentration of the user indicative of onset of a physiological event.

22. The method according to claim 21, wherein the step of detecting comprises measuring the hearing threshold of the user to the audio output.

23. The method according to claim 22, further including comparing the detected hearing threshold to a reference threshold.

24. The method of claim 23, wherein the reference threshold comprises one or more reference threshold values obtained from the user.

25. The method according to claim 23, wherein the reference threshold comprises one or more reference threshold values statistically determined to represent a typical average user in a particular hormonal state.

26. The method according to claim 23, wherein the step of comparing is utilized to detect a change of hearing sensitivity in the user.

27. The method according to claim 26, further including determining the degree of the change of hearing sensitivity to determine the hormonal state of the user.

28. The method according to claim 23, wherein the step of comparing is performed sequentially.

29. The method according to claim 22, wherein the hearing threshold of the user is measured at predetermined intervals to provide a series of measurements which are utilized to form baseline or reference threshold measurements to which subsequent measurements from the user are compared.

30. The method according to claim 29, further including utilizing an indication of a predetermined reduction in hearing sensitivity of the user to predict a change in hormonal concentration.

31. The method according to claim 21, wherein the step of detecting comprises sensing ability of the user to synthesize binaural beats.

32. The method of claim 27, wherein at least one step is performed by a computer.

33. The method of claim 21, wherein the step of applying utilizes a telephone, a headset or ear phones.

34. A device for detecting a change in a psycho-acoustic sensitivity of a user caused by a hormonal concentration change in the user indicative of onset of a physiological event, the device comprising:
audiometric means for obtaining a measurement of a present psycho-acoustic response of the user and for providing an output representative of the present measurement;
means operatively connected to the audiometric means for storing the present measurement and for storing reference psycho-acoustic response values;
means operatively connected to the audiometric means and to the storing means for comparing the present measurement with the reference psycho-acoustic response values such that the hormonal state of the user may be ascertained, the means for comparing including an output representative of the hormonal state of the user;
means connected to the comparing means for utilizing the output to enable the hormonal state of the user to be ascertained to indicate onset of a physiological event.

35. The device of claim 34, wherein the audiometric means, the storing means, the comparing means or the utilizing means comprises a computer.

36. A device for detecting a change in binaural beat synthesis ability of a user caused by a hormonal concentration change in the user comprising:
means for generating first and second pure audio tones each in a frequency range of from out 100 Hz to about 1000 Hz and such that the first tone differs in frequency from the second tone in an amount from about 1 Hz to about 60 Hz;

means for delivering said first and second audio tones simultaneously to the ears of the user;

signalling means operable by the user for providing a signal when the user has lost psycho-acoustic ability to synthesize binaural beats; and means operatively connected to the signalling means for utilizing the signal to provide an indication of a hormonal concentration change in the user.

37. The device according to claim 36, wherein the means for utilizing the signal includes means for comparing the present measured beat synthesis ability of the user to reference values of ability representing beat synthesis at various stages of hormonal concentration change to provide an indication of the present hormonal concentration state of the user.

38. The device of claim 36, wherein means for generating, means for delivering, the signalling means or means for utilizing comprises a computer.

* * * * *